United States Patent
Sluss et al.

(10) Patent No.: US 9,468,577 B2
(45) Date of Patent: Oct. 18, 2016

(54) PERINEAL POST PAD FOR PATIENT LOWER EXTREMITY POSITIONING SYSTEMS

(71) Applicant: ARTHREX, INC., Naples, FL (US)

(72) Inventors: Robert K. Sluss, Naples, FL (US); Michael Gerhardt, Santa Monica, CA (US)

(73) Assignee: Arthrex, Inc., Naples, FL (US)

( * ) Notice: Subject to any disclaimer, the term of this patent is extended or adjusted under 35 U.S.C. 154(b) by 280 days.

(21) Appl. No.: 13/760,741

(22) Filed: Feb. 6, 2013

(65) Prior Publication Data

US 2013/0199541 A1    Aug. 8, 2013

Related U.S. Application Data

(60) Provisional application No. 61/595,417, filed on Feb. 6, 2012.

(51) Int. Cl.
*A47B 7/00*    (2006.01)
*A47C 17/86*    (2006.01)
(Continued)

(52) U.S. Cl.
CPC ............ *A61G 15/12* (2013.01); *A61F 5/00* (2013.01); *A61F 5/04* (2013.01); *A61F 5/042* (2013.01);
(Continued)

(58) Field of Classification Search
CPC ........ A61G 7/00; A61G 7/002; A61G 7/015; A61G 7/05; A61G 7/1073; A61G 7/1082; A61G 7/1088; A61G 7/109; A61G 7/1096; A61G 13/00; A61G 13/0036; A61G 13/02; A61G 13/12; A61G 13/1205; A61G 13/123; A61G 13/126; A61F 5/00; A61F 5/37; A61F 5/04; A61F 5/042; A61F 7/00; A61F 2007/0039; A61F 2007/004; A61F 2007/0048; A61H 1/00; A61H 1/02; A61H 1/0218; A61H 1/0222; A61H 1/0237; A61H 1/0244; A61H 2001/0248; A61H 1/0255
USPC ........... 5/613, 621, 624, 634, 648, 658, 655, 5/655.9, 953; 128/846, 869, 870, 871, 128/882, 883; 602/23, 24, 32–36, 40
See application file for complete search history.

(56) References Cited

U.S. PATENT DOCUMENTS 2,691,979 A * 10/1954 Watson ........................... 602/39
5,515,562 A * 5/1996 Miller et al. ...................... 5/624
(Continued)

FOREIGN PATENT DOCUMENTS

WO        2013/112879 A1    8/2013

OTHER PUBLICATIONS

European Patent Office, "European search report and European search opinion," a document of 6 pages, dated Nov. 8, 2013.
(Continued)

*Primary Examiner* — Justine Yu
*Assistant Examiner* — Brandon L Jackson
(74) *Attorney, Agent, or Firm* — Akerman LLP; Michael K. Dixon

(57) ABSTRACT

A patient lower extremity positioning system that is configured to facilitate easier use of surgical instruments during open and arthroscopic procedures of the lower extremity, including, but not limited to the hip joint, acetabulum, femur, femoral neck and femoral shaft is disclosed. The patient lower extremity positioning system may include one or more perineal pads configured to be supported adjacent to a patient torso support such that the perineal pad is positionable adjacent to a patient's perineum. The perineal pad may be formed from a perineal pad body coupled to a distal transition section extending distally from the perineal pad body. The distal transition section may have a distal tip with a cross-sectional area that is less than a cross-sectional area of the perineal pad body, thereby enabling a surgeon to more easily position surgical instruments during surgery without the perineal pad conflicting with the surgical instruments.

15 Claims, 5 Drawing Sheets

(51) Int. Cl.

| | | |
|---|---|---|
| *A47C 31/00* | (2006.01) | |
| *A61F 5/37* | (2006.01) | |
| *A61F 13/00* | (2006.01) | |
| *A61B 19/00* | (2006.01) | |
| *A61F 5/00* | (2006.01) | |
| *A61G 15/12* | (2006.01) | |
| *A61G 13/12* | (2006.01) | |
| *A61G 7/10* | (2006.01) | |
| *A61G 13/02* | (2006.01) | |
| *A61G 7/05* | (2006.01) | |
| *A61G 7/015* | (2006.01) | |
| *A61G 7/00* | (2006.01) | |
| *A61G 13/00* | (2006.01) | |
| *A61G 7/002* | (2006.01) | |
| *A61H 1/02* | (2006.01) | |
| *A61F 5/04* | (2006.01) | |
| *A61F 5/042* | (2006.01) | |
| *A61H 1/00* | (2006.01) | |

(52) U.S. Cl.
CPC . *A61F 5/37* (2013.01); *A61G 7/00* (2013.01); *A61G 7/002* (2013.01); *A61G 7/015* (2013.01); *A61G 7/05* (2013.01); *A61G 7/109* (2013.01); *A61G 7/1073* (2013.01); *A61G 7/1082* (2013.01); *A61G 7/1088* (2013.01); *A61G 7/1096* (2013.01); *A61G 13/00* (2013.01); *A61G 13/0036* (2013.01); *A61G 13/02* (2013.01); *A61G 13/12* (2013.01); *A61G 13/123* (2013.01); *A61G 13/1205* (2013.01); *A61H 1/00* (2013.01); *A61H 1/02* (2013.01); *A61H 1/0218* (2013.01); *A61H 1/0222* (2013.01); *A61H 1/0237* (2013.01); *A61H 1/0244* (2013.01); *A61G 2013/0081* (2013.01)

(56) References Cited

U.S. PATENT DOCUMENTS

| | | | | |
|---|---|---|---|---|
| 7,246,390 | B2* | 7/2007 | Mitsuishi et al. | 5/648 |
| 7,947,006 | B2* | 5/2011 | Torrie et al. | 602/32 |
| 8,683,631 | B2* | 4/2014 | Bellows et al. | 5/624 |
| 2004/0133979 | A1* | 7/2004 | Newkirk et al. | 5/600 |
| 2004/0133983 | A1* | 7/2004 | Newkirk et al. | 5/624 |
| 2007/0251011 | A1* | 11/2007 | Matta et al. | 5/624 |
| 2007/0265635 | A1 | 11/2007 | Torrie et al. | |
| 2011/0023893 | A1* | 2/2011 | Striggow et al. | 128/882 |
| 2011/0099720 | A1 | 5/2011 | Wyslucha et al. | |

OTHER PUBLICATIONS

European Patent Office, "European search report and European search opinion," a document of 4 pages, dated Jun. 1, 2015.

* cited by examiner

PERINEAL POST PAD FOR PATIENT LOWER EXTREMITY POSITIONING SYSTEMS

CROSS-REFERENCE TO RELATED APPLICATION

This application claims the benefit of U.S. provisional patent application Ser. No. 61/595,417, filed on Feb. 6, 2012.

FIELD OF THE INVENTION

The invention relates to patient lower extremity positioning systems, and more particularly, to support components of patient lower extremity positioning systems.

BACKGROUND

During open and arthroscopic surgical procedures of the lower extremity, such as the hip joint, acetabulum, femur, femoral neck and femoral shaft, a lower extremity distraction and positioned system is often used to distract the femoral head out of the acetabulum or is used to reduce the forces across a fracture site. These distraction and positioning systems are generally classified into two groups, including: fully functional tables with leg spars and table attachment units that are attached to traditional operating room tables. Patients are generally placed in these systems in the supine or lateral decubitus position. Once in the distraction system, the patient's feet and legs are mounted into specialized boots or connection points and the patient's groin or perineal area rests against a large post. Once gross and fine distraction are placed on the operative and nonoperative legs, the post acts as a fulcrum to stabilize the pelvis and allow the leg to be distracted without the patient slipping off the table platform. Once leg traction is achieved, the surgeon begins the procedure, which generally is in the anterior and lateral portion of the pelvis and hip joint. If the surgeon needs to bring an instrument towards the midline of the patient, the instrument would be prevented from such movement by the post. The instrument would contact the post, thereby preventing necessary movement.

SUMMARY OF THE INVENTION

A patient lower extremity positioning system that is configured to facilitate easier use of surgical instruments during open and arthroscopic procedures of the lower extremity, including, but not limited to the hip joint, acetabulum, femur, femoral neck and femoral shaft is disclosed. The patient lower extremity positioning system may include one or more perineal pads configured to be supported adjacent to a patient torso support such that the perineal pad is positionable adjacent to a patient's perineum. The perineal pad may be formed from a perineal pad body coupled to a distal transition section extending distally from the perineal pad body. The distal transition section may have a distal tip with a cross-sectional area that is less than a cross-sectional area of the perineal pad body at an intersection of the distal transition section and the perineal pad body. In such a position, a surgeon may more easily position surgical instruments during surgery without the perineal pad conflicting with the surgical instruments.

In at least one embodiment, the patient lower extremity positioning system may be formed from one or more perineal pads formed from a perineal pad body coupled to a distal transition section extending distally from the perineal pad body. The distal transition section may have a distal tip with a cross-sectional area that is less than a cross-sectional area of the perineal pad body at an intersection of the distal transition section and the perineal pad body. The perineal pad may be configured to be supported adjacent to a patient torso support such that the perineal pad is positionable adjacent to a patient's perineum. The distal transition section of the perineal pad may be generally conical. The distal transition section may have a length that is less than about half of a total length of the perineal pad. In another embodiment, the distal transition section may have a length that is greater than about one quarter of the total length of the perineal pad.

The perineal pad body may be generally cylindrical or have another shape. The cross-sectional area of the perineal pad body at an intersection of the distal transition section and the perineal pad body may be generally equal to a cross-sectional area of the perineal pad body at a proximal end. The perineal pad body may also include a support receiving chamber extending longitudinally from a proximal end of the perineal pad into the perineal pad body. The support receiving chamber may be generally cylindrical or have another shape. The support receiving chamber may extend completely through the perineal pad body and the distal transition section from the distal tip to a proximal end of the perineal pad body.

A torso support system may be coupled to the perineal pad and configured to support a torso of a patient. The torso support system may include a table to which the perineal pad is attached. The torso support system may also include one or more leg spars attached to the table. The leg spar may be releasably attached to the table. The torso support system may also be formed from two leg spars attached to the table. The torso support system may include one or more attachment systems configured to be attached to a table.

An advantage of this invention is that perineal pad frees up an area of the sterile field that allows for greater freedom of motion of instruments being used during open and arthroscopic hip surgical procedures in which a lower extremity distraction and positioning system is used.

These and other embodiments are described in more detail below.

DETAILED DESCRIPTION OF THE FIGURES

Figure 1:
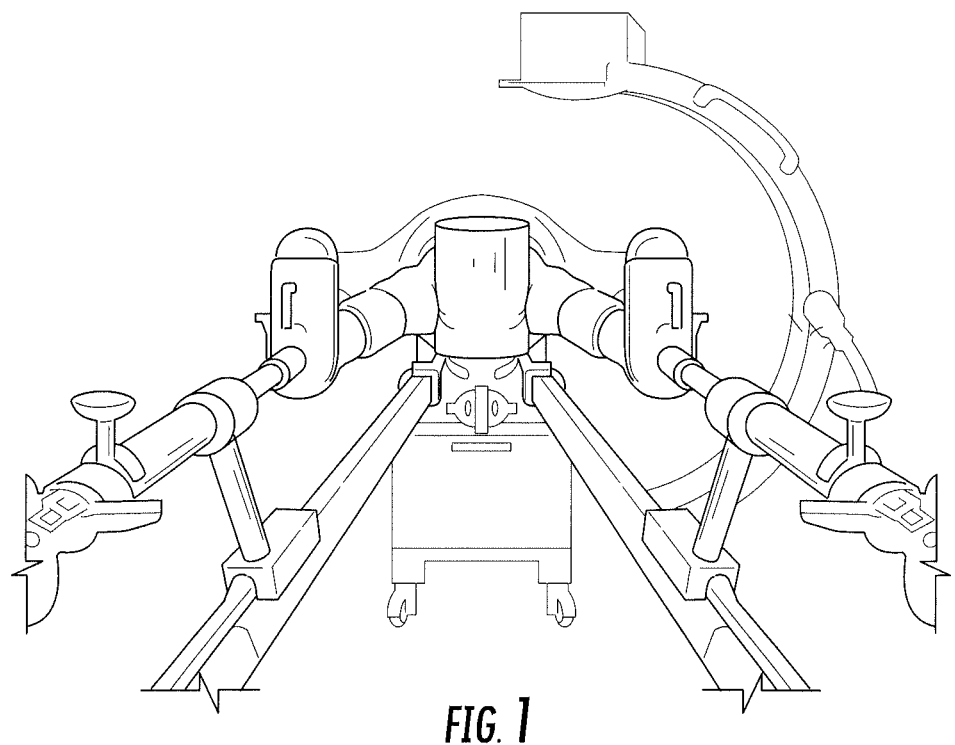
FIG. 1 is a perspective view of a conventional lower extremity positioning system.
Figure 2:
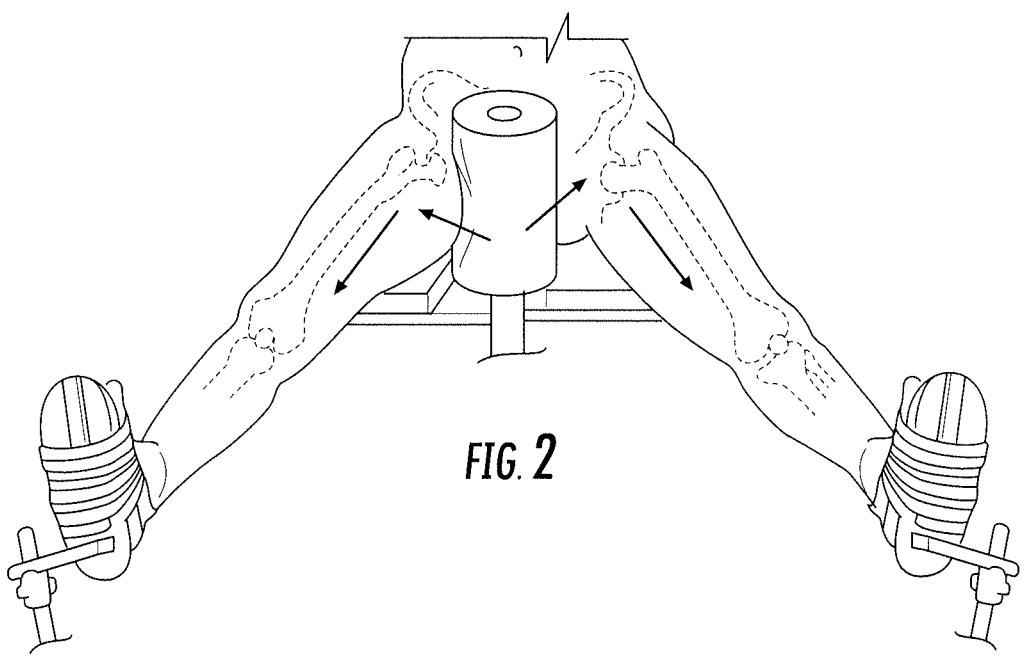
FIG. 2 is a perspective view of another conventional lower extremity positioning system.
Figure 3:
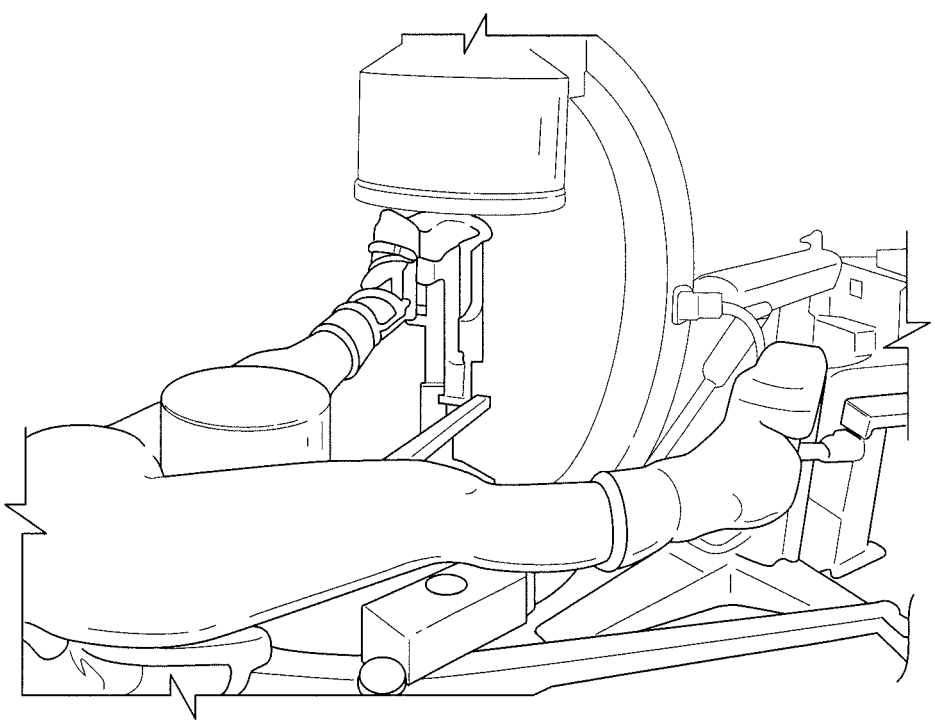
FIG. 3 is a perspective view of a patient supported by a conventional lower extremity positioning system.
Figure 4:
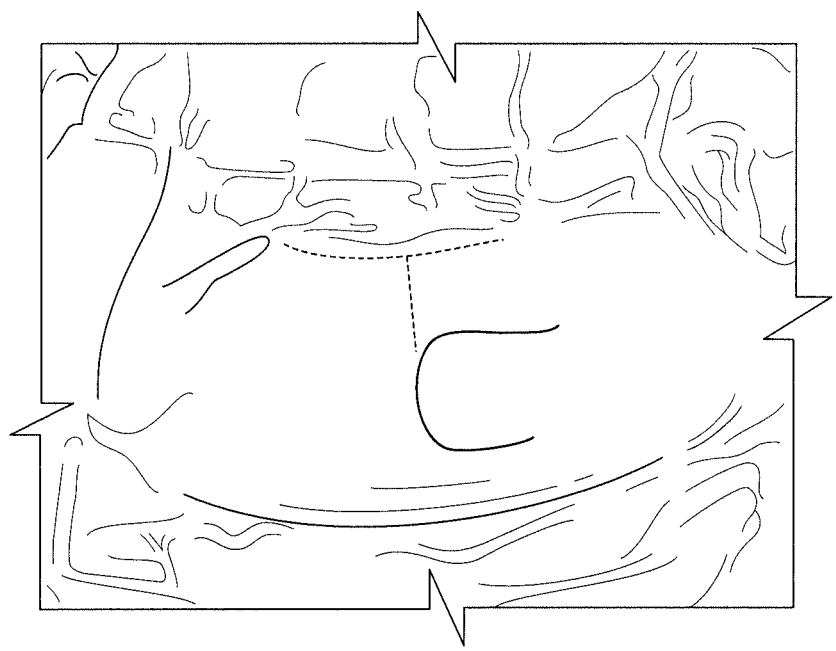
FIG. 4 is a top view of a patient with markings identifying the location for incision at the intersection of the dotted lines.
Figure 5:
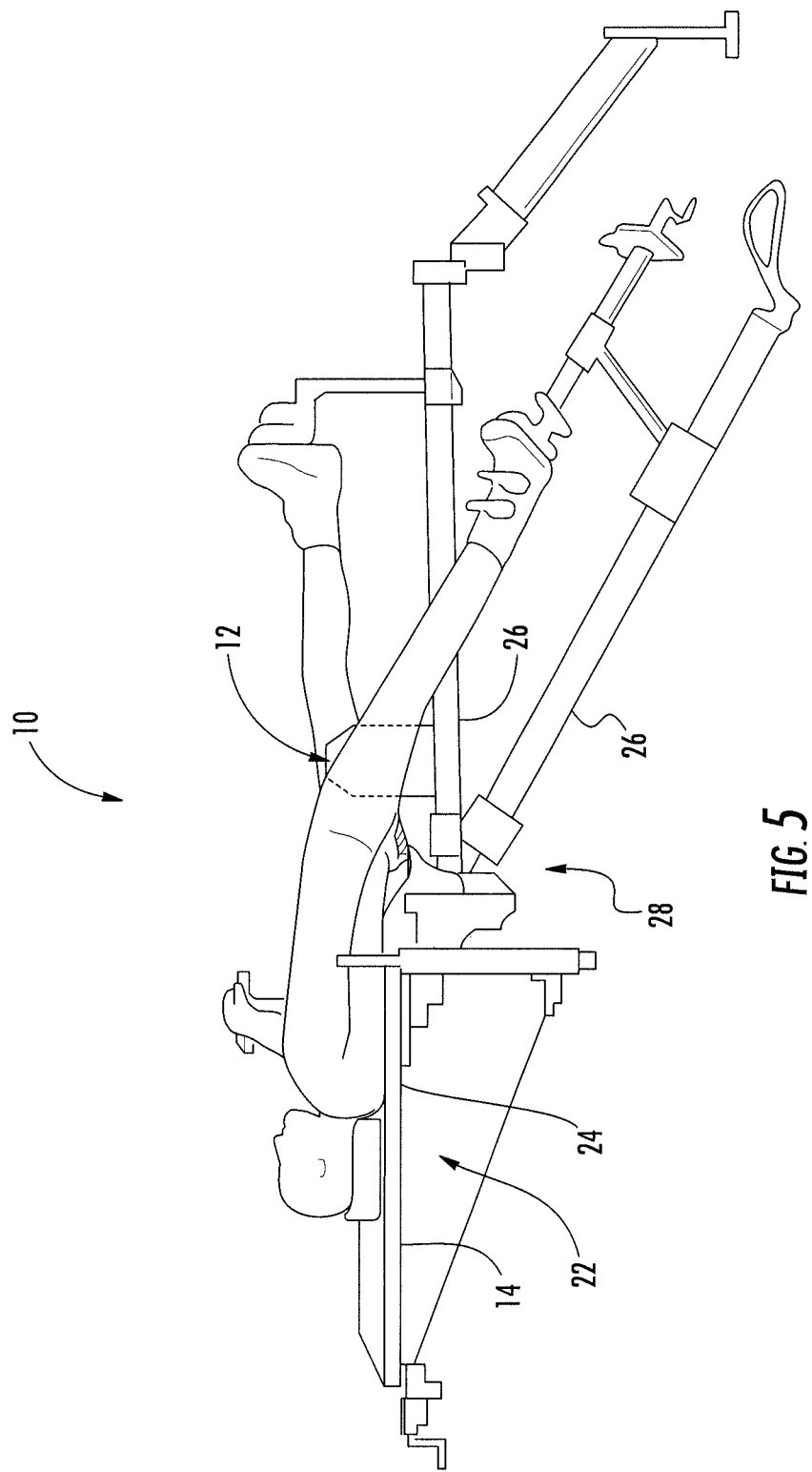
FIG. 5 is a side view of a patient positioned in a patient lower extremity positioning system of this invention.
Figure 6:
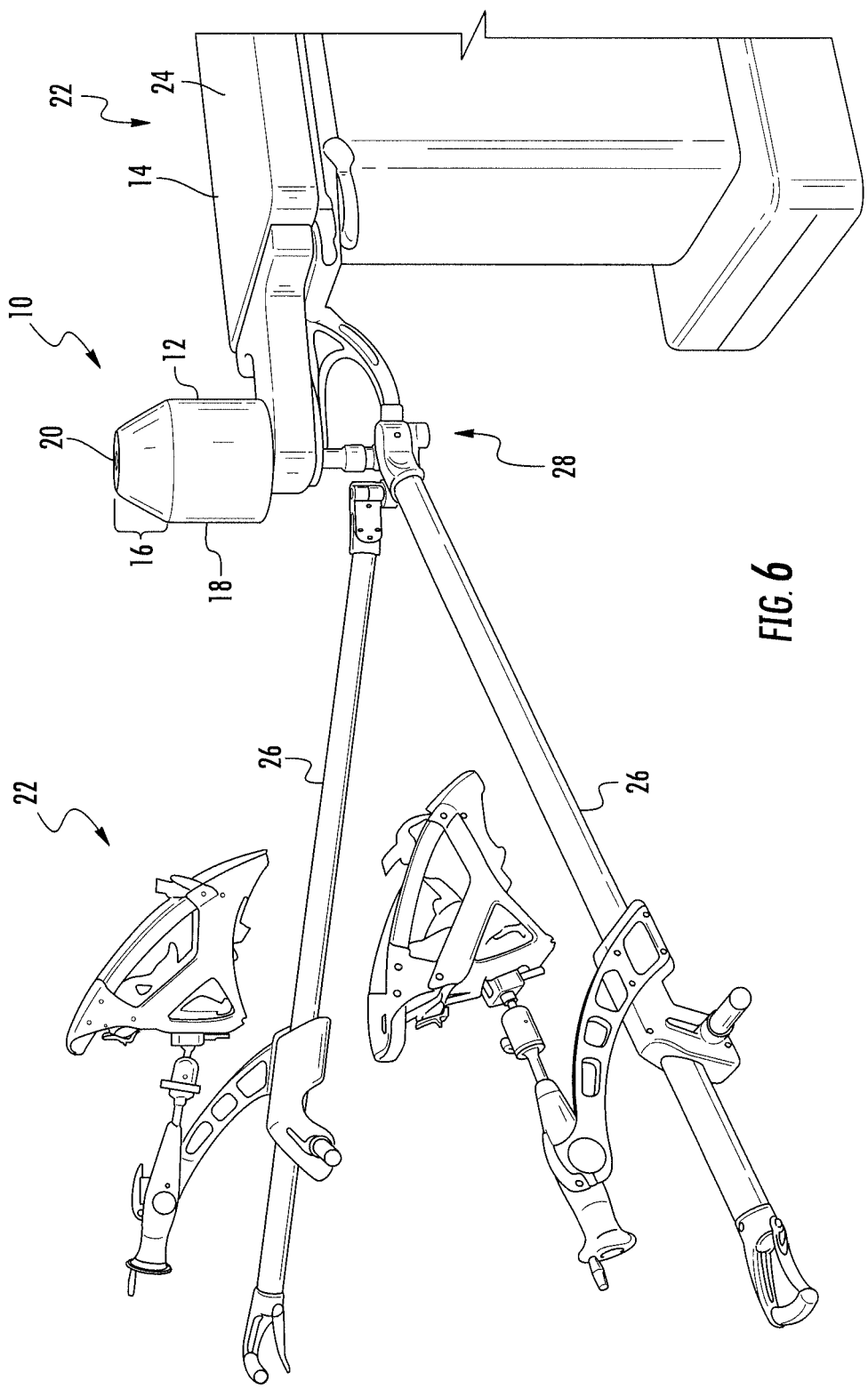
FIG. 6 is a perspective view of the patient lower extremity positioning system of this invention.
Figure 7:
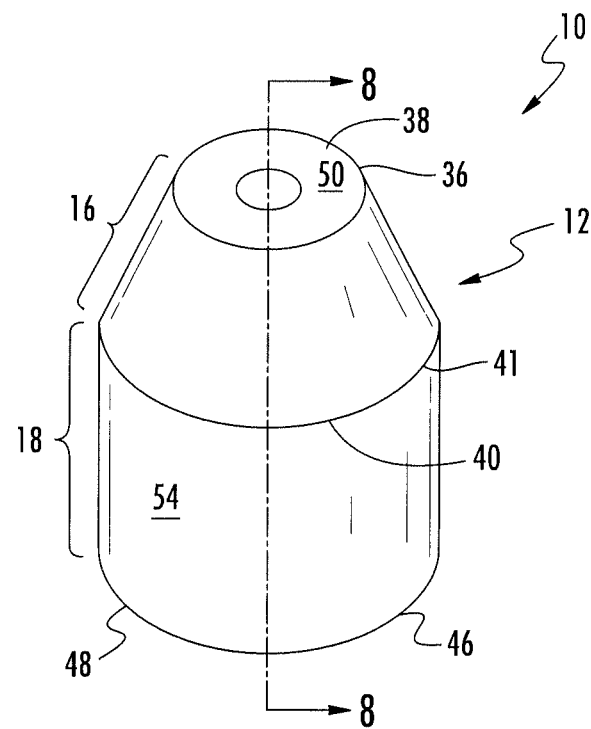
FIG. 7 is a perspective view of the perineal pad of the patient lower extremity positioning system.
Figure 8:
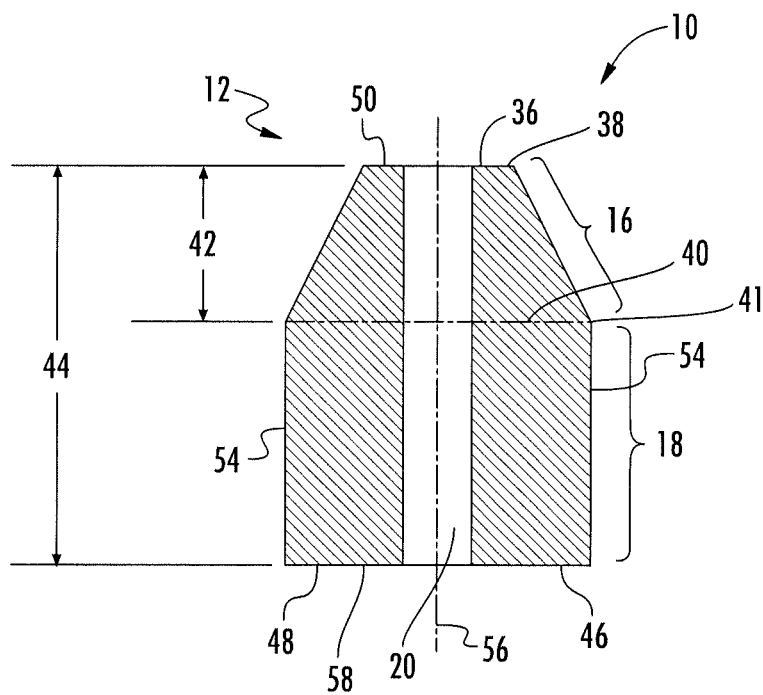
FIG. 8 is a cross-sectional view of the perineal pad taken at section line 8-8 of FIG. 7.

As shown in FIGS. 5-8, a patient lower extremity positioning system 10 that is configured to facilitate easier use of surgical instruments during open and arthroscopic procedures of the lower extremity, including, but not limited to the hip joint, acetabulum, femur, femoral neck and femoral shaft is disclosed. The patient lower extremity positioning system 10 may include one or more perineal pads 12 configured to be supported adjacent to a patient torso support 14 such that the perineal pad 12 is positionable adjacent to a patient's perineum. The perineal pad 12 may be formed from a perineal pad body 18 coupled to a distal transition section 16 extending distally from the perineal pad body 18. The distal transition section 16 may have a distal tip 36 with a cross-sectional area 38 that is less than a cross-sectional area 40 of the perineal pad body 18 at an intersection 42 of the distal transition section 16 and the perineal pad body 18. In such a position, a surgeon may more easily position surgical instruments during surgery without the perineal pad 12 conflicting with the surgical instruments.

The distal transition section 16 of the perineal pad 12 may have any appropriate configuration enabling the perineal pad 12 to be used without interfering with an instrument used by a surgeon. In at least one embodiment, the distal transition section 16 of the perineal pad 12 may be generally conical. The distal transition section 16 may have a length 42 that is less than about half of a total length 44 of the at least one perineal pad 12. Alternatively, the distal transition section 16 may have a length 42 that is less than about one third of the total length 44 of the perineal pad 12. The distal transition section 16 may also have a length 42 that is greater than about one quarter of the total length 44 of the perineal pad 12. The perineal pad 12 may be formed from any appropriate material, such as, but not limited to, foam, plastic, and fabric covered foam.

The perineal pad body 18 may have any appropriate configuration enabling the perineal pad 12 to be used without interfering with a surgeon. In at least one embodiment, the perineal pad body 18 may be generally cylindrical. The cross-sectional area 38 of the perineal pad body 18 at an intersection 41 of the distal transition section 16 and the perineal pad body 18 is generally equal to a cross-sectional area 46 of the perineal pad body 18 at a proximal end 48. A support receiving chamber 20 may extend longitudinally into the perineal pad 12 from the proximal end 48 into the perineal pad body 18. The support receiving chamber 20 may be generally cylindrical or have another appropriate shape. The support receiving chamber 20 may extend completely through the perineal pad body 18 and the distal transition section 16 from an outer surface 50 the distal tip 36 to the proximal end 48 of the perineal pad body 18. The support receiving chamber 20 may be centrally positioned within the perineal pad body 18. In other embodiments, the support receiving chamber 20 may be offset within the perineal pad body 18, thereby enabling the support receiving chamber 20 to be used to position a patient differently based upon the rotational position of the perineal pad body 18 relative to a post to which the pad 12 is attached. The perineal pad body 18 may have a generally consistent cross-sectional area and cross-sectional configuration. An outer surface 54 of the perineal pad body 18 may be generally aligned with a longitudinal axis 56 of the perineal pad body 18. In other embodiments, the outer surface 54 of the perineal pad body 18 may be skewed relative to the longitudinal axis 56 of the perineal pad body 18. The outer surface 50 of the distal tip 36 may be generally parallel to an outer surface 48 of the proximal end 48. In other embodiments, the outer surface 50 of the distal tip 36 may be nonparallel to an outer surface 48 of the proximal end 48.

The patient lower extremity positioning system 10 may also include a torso support system 22 coupled to perineal pad 12 and configured to support a torso of a patient. In one embodiment, the torso support system 22 may be a table 24 to which the perineal pad 12 may be attached. The table 24 may be formed from one or more materials, such as, but not limited to, one or more metals, such as stainless steel, aluminum, titanium, silver, platinum and the like, plastics, rubber and wood.

One or more leg spars 26 may be attached to the table 24. The leg spars 26 may be releasably attached to the table 24. The position of the leg spars 26 relative to the table 24 may be adjusted. In particular, the distance between the foot receivers and the perineal pad 12 may be changed to accommodate the differences in leg lengths between patients. In one embodiment, the leg spar 26 may be formed from two leg spars 26 attached to the table 24. In another embodiment, the torso support system 22 may include an attachment system 28 configured to be attached to a table, such as an existing table in place in an operating room or the like.

During use, the patient lower extremity positioning system 10 may be used during open and arthroscopic procedures of the lower extremity, including, but not limited to the hip joint, acetabulum, femur, femoral neck and femoral shaft to distract the femoral head out of the acetabulum or reduce the forces across a fracture site. A patient may be placed such that the perineal pad 12 is placed between the legs of a patient where the patient's perineum is in contact with the perineal pad 12 or in close proximity to the perineal pad 12. Patients may be placed onto the patient lower extremity positioning system 10 in the supine or lateral decubitus position. Once in the patient lower extremity positioning system 10, a patient's feet and legs may be positioned in connection systems, such as, but not limited to, boots, and the patient's groin rests against the perineal pad 12, which may be attached to a post. Once gross and fine distraction are placed on the operative and nonoperative legs, the perineal post and pad act as a fulcrum to stabilize the pelvis and allow the leg to be distracted without the patient slipping off the torso support system 22. Once leg traction has been achieved, the surgeon may begin a procedure, which typically is in the anterior and lateral portion of the pelvis and hip joint. Should the surgeon need to move an instrument near a midline of the patient, the surgeon may do so without having the perineal pad 12 in the way of the instrument because of the existence of the distal transition section 16 of the perineal pad 12. By incorporating the distal transition section 16, the top of the perineal pad 12 has a reduced cross-sectional area that allows midline or medial motion of instruments in the sterile field.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A patient lower extremity positioning system, comprising:
    at least one perineal pad formed from a perineal pad body coupled to a distal transition section extending distally from the perineal pad body;
    wherein the distal transition section has a distal tip with a cross-sectional area that is less than a cross-sectional area of the perineal pad body at an intersection of the distal transition section and the perineal pad body;

wherein the at least one perineal pad is configured to be supported adjacent to a patient torso support such that the perineal pad is positionable adjacent to a patient's perineum;

wherein the distal transition section of the at least one perineal pad is generally conical;

wherein the distal transition section has a length that is greater than about one quarter of a total length of the at least one perineal pad;

wherein the distal transition section has a length that is less than about half of a total length of the at least one perineal pad;

wherein a diameter of an outer tip of the distal transition section is less than half of a diameter of the perineal pad body; and wherein the distal transition section is configured such that an outer surface forming the distal transition section forms a linear line extending from the perineal pad body to an outer tip of the distal transition section when viewed in cross-section from a cross-sectional cut made from the outer tip of the distal transition section to a proximal end of the perineal pad body along a longitudinal axis of the at least one perineal pad and viewed orthogonal to a longitudinal axis of the at least one perineal pad.

2. The patient lower extremity positioning system of claim 1, further comprising a torso support system coupled to the at least one perineal pad and configured to support a torso of a patient.

3. The patient lower extremity positioning system of claim 2, wherein the torso support system is comprised of a table to which the at least one perineal pad is attached.

4. The patient lower extremity positioning system of claim 3, further comprising at least one leg spar attached to the table.

5. The patient lower extremity positioning system of claim 4, wherein the at least one leg spar is releasably attached to the table.

6. The patient lower extremity positioning system of claim 4, wherein the at least one leg spar is formed from two leg spars attached to the table.

7. The patient lower extremity positioning system of claim 2, wherein the torso support system includes at least one attachment system configured to be attached to a table.

8. The patient lower extremity positioning system of claim 1, further comprising a support receiving chamber extending longitudinally from a proximal end of the at least one perineal pad into the perineal pad body.

9. The patient lower extremity positioning system of claim 8, wherein the support receiving chamber is generally cylindrical.

10. The patient lower extremity positioning system of claim 8, wherein the support receiving chamber extends completely through the perineal pad body and the distal transition section from the distal tip to a proximal end of the perineal pad body.

11. The patient lower extremity positioning system of claim 1, wherein the perineal pad body is generally cylindrical and wherein the cross-sectional area of the perineal pad body at an intersection of the distal transition section and the perineal pad body is generally equal to a cross-sectional area of the perineal pad body at a proximal end.

12. A patient lower extremity positioning system, comprising:
at least one perineal pad formed from a perineal pad body coupled to a distal transition section extending distally from the perineal pad body;

wherein the distal transition section has a distal tip with a cross-sectional area that is less than a cross-sectional area of the perineal pad body at an intersection of the distal transition section and the perineal pad body; and wherein the at least one perineal pad is configured to be supported adjacent to a patient torso support such that the perineal pad is positionable adjacent to a patient's perineum;

wherein the perineal pad body is generally cylindrical and wherein the cross-sectional area of the perineal pad body at an intersection of the distal transition section and the perineal pad body is generally equal to a cross-sectional area of the perineal pad body at a proximal end;

a support receiving chamber extending longitudinally from a proximal end of the at least one perineal pad into the perineal pad body;

wherein the distal transition section of the at least one perineal pad is generally conical;

wherein the distal transition section has a length that is greater than about one quarter of a total length of the at least one perineal pad;

wherein the distal transition section has a length that is less than about half of a total length of the at least one perineal pad;

wherein a diameter of an outer tip of the distal transition section is less than half of a diameter of the perineal pad body; and wherein the distal transition section is configured such that an outer surface forming the distal transition section forms a linear line extending from the perineal pad body to an outer tip of the distal transition section when viewed in cross-section from a cross-sectional cut made from the outer tip of the distal transition section to a proximal end of the perineal pad body along a longitudinal axis of the at least one perineal pad and viewed orthogonal to a longitudinal axis of the at least one perineal pad.

13. The patient lower extremity positioning system of claim 12, wherein the support receiving chamber is generally cylindrical and extends completely through the perineal pad body and the distal transition section from the distal tip to a proximal end of the perineal pad body.

14. The patient lower extremity positioning system of claim 12, further comprising a torso support system coupled to the at least one perineal pad and configured to support a torso of a patient, wherein the torso support system includes at least one attachment system configured to be attached to a table and at least one leg spar releasably attached to the table.

15. A patient lower extremity positioning system, comprising:
at least one perineal pad formed from a perineal pad body coupled to a distal transition section extending distally from the perineal pad body;

wherein the distal transition section has a distal tip with a cross-sectional area that is less than a cross-sectional area of the perineal pad body at an intersection of the distal transition section and the perineal pad body; and wherein the at least one perineal pad is configured to be supported adjacent to a patient torso support such that the perineal pad is positionable adjacent to a patient's perineum;

wherein the perineal pad body is generally cylindrical and wherein the cross-sectional area of the perineal pad body at an intersection of the distal transition section and the perineal pad body is generally equal to a cross-sectional area of the perineal pad body at a proximal end;

wherein the distal transition section of the at least one perineal pad is generally conical;

wherein the distal transition section has a length that is less than about half of a total length of the at least one perineal pad and greater than about one quarter of a total length of the at least one perineal pad;

a support receiving chamber extending longitudinally from a proximal end of the at least one perineal pad into the perineal pad body and wherein the support receiving chamber is generally cylindrical;

wherein a diameter of an outer tip of the distal transition section is less than half of a diameter of the perineal pad body; and wherein the distal transition section is configured such that an outer surface forming the distal transition section forms a linear line extending from the perineal pad body to an outer tip of the distal transition section when viewed in cross-section from a cross-sectional cut made from the outer tip of the distal transition section to a proximal end of the perineal pad body along a longitudinal axis of the at least one perineal pad and viewed orthogonal to a longitudinal axis of the at least one perineal pad.

* * * * *